United States Patent [19]
Kubnick

[11] Patent Number: 4,479,738
[45] Date of Patent: Oct. 30, 1984

[54] ATTACHING ASSEMBLY
[75] Inventor: Norman R. Kubnick, Skokie, Ill.
[73] Assignee: Sellstrom Manufacturing Company, Palatine, Ill.
[21] Appl. No.: 489,048
[22] Filed: Apr. 27, 1983
[51] Int. Cl.³ .............................................. B25G 3/00
[52] U.S. Cl. .................................... 403/407; 403/410; 2/10; 2/424
[58] Field of Search ................. 2/8, 10, 424; 403/410, 403/407

[56] References Cited
U.S. PATENT DOCUMENTS

| | | | |
|---|---|---|---|
| 2,904,790 | 9/1959 | Ruggiero | 2/8 |
| 3,021,527 | 2/1962 | Larsen | 2/10 X |
| 3,137,005 | 6/1964 | Herbine et al. | 2/10 |
| 3,375,529 | 4/1968 | Timm et al. | 2/8 |
| 4,109,320 | 8/1978 | Anderson | 2/10 |

Primary Examiner—Andrew V. Kundrat
Attorney, Agent, or Firm—Neuman, Williams, Anderson & Olson

[57] ABSTRACT

An assembly is provided for use in securing a secondary unit, such as a welder's mask or the like, to a primary unit, such as a protective helmet often referred to as a hard hat. The secondary unit is mounted for adjustment between operative and inoperative modes relative to the primary unit. The primary unit is provided with at least one exterior shoulder projecting laterally outwardly from a wall surface. The shoulder is provided with an upwardly extending passageway. The assembly includes a base portion which rests upon and is supported by the shoulder. Connected to and depending from the base portion are a plurality of fingers which extend into and resiliently engage the shoulder passageway and retain the bracket in assembled relation with the primary unit. Adjustable means coact with the base portion to secure the secondary unit to the bracket base portion whereby the secondary unit can assume a selected mode relative to the primary unit.

3 Claims, 9 Drawing Figures

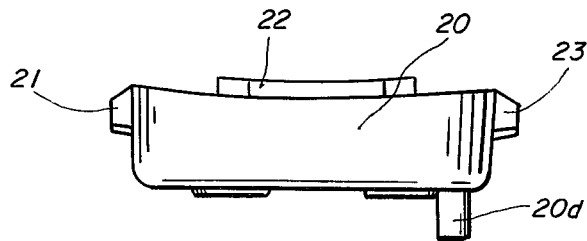
FIG. 8
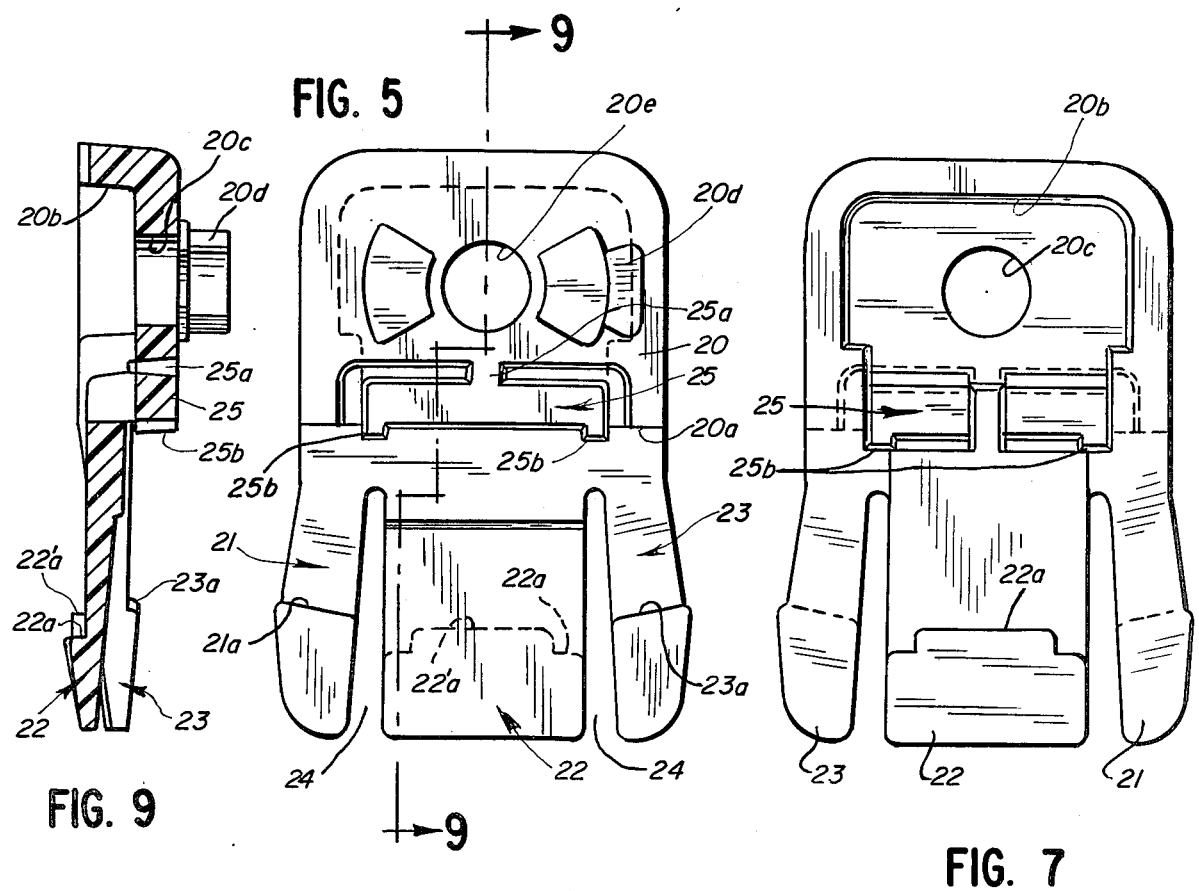
FIG. 5
FIG. 7
FIG. 9
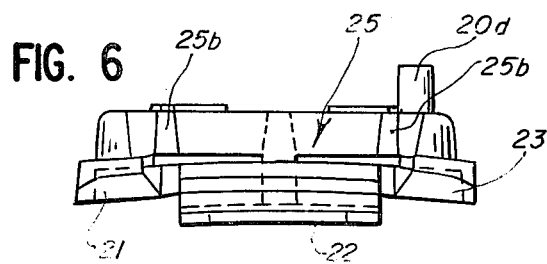
FIG. 6

ATTACHING ASSEMBLY

BACKGROUND OF THE INVENTION

Various devices have heretofore been provided for attaching an adjustable mask, telephone communication components, or the like to a hard hat or protective helmet; however, because of certain design characteristics inherent in such devices and/or hard hats, the attaching assemblies or devices were beset with one or more of the following shortcomings: (a) the attachment between the mask and hat was insecure and unstable and therefore did not provide the desired protection to, or utility for, the wearer; (b) it was a difficult and awkward manipulation to attach the device to the hard hat; (c) the device embodied an inordinate number of components; and (d) the device was of costly, complex and fragile construction and susceptible to malfunction.

SUMMARY OF THE INVENTION

Thus, it is an object of the invention to provide an attaching assembly which effectively overcomes the aforementioned shortcomings associated with prior devices of this general type.

It is a further object to provide an attaching assembly which is capable of accommodating a wide variety of secondary units.

It is a still further object to provide an attaching assembly of rugged construction and one which is not adversely affected by extreme climatic conditions.

It is a still further object to provide an attaching assembly which is easy to attach to or detach from a hard hat and does not require an inordinate amount of manual effort to perform such manipulations.

Further and additional objects will appear from the description, accompanying drawings and appended claims.

In accordance with one embodiment of the invention, an attaching assembly of the type described is provided which is adapted to be removably mounted on an exterior shoulder formed on a primary unit and extending laterally outwardly from an exterior wall surface thereof. Normally, when the primary unit is a hard hat or helmet, a pair of shoulders are provided on opposite sides of the hat in the vicinity of the ears of the wearer. Each shoulder is provided with an upwardly extending passageway. Removably mounted on each shoulder is an attaching assembly which includes a bracket having a base portion with a plurality of fingers connected thereto and depending therefrom. The fingers are inserted into and resiliently engage the shoulder passageway and retain the bracket in assembled relation with the primary unit. The base portion is provided with a stabilizing means which is disposed adjacent the connection between the base portion and the depending fingers. When the bracket is assembled on the shoulder, the stabilizing means will resiliently engage the surface of the shoulder circumjacent the upper end of the passageway. Each assembly also includes an adjustable means which coacts with the bracket base portion and secures thereto the secondary unit.

DESCRIPTION

For a more complete understanding of the invention reference should be made to the drawings wherein:

FIG. 5 is an enlarged front view of the bracket per se shown in FIG. 3.

FIG. 6 is a bottom view of the bracket shown in FIG. 5.

FIG. 7 is a back view of the bracket shown in FIG. 5.

Fig. 8 is a top view of the bracket shown in FIG. 5.

FIG. 9 is a sectional view taken along line 9—9 of FIG. 5.

Figures 1, 2, 3, 4:
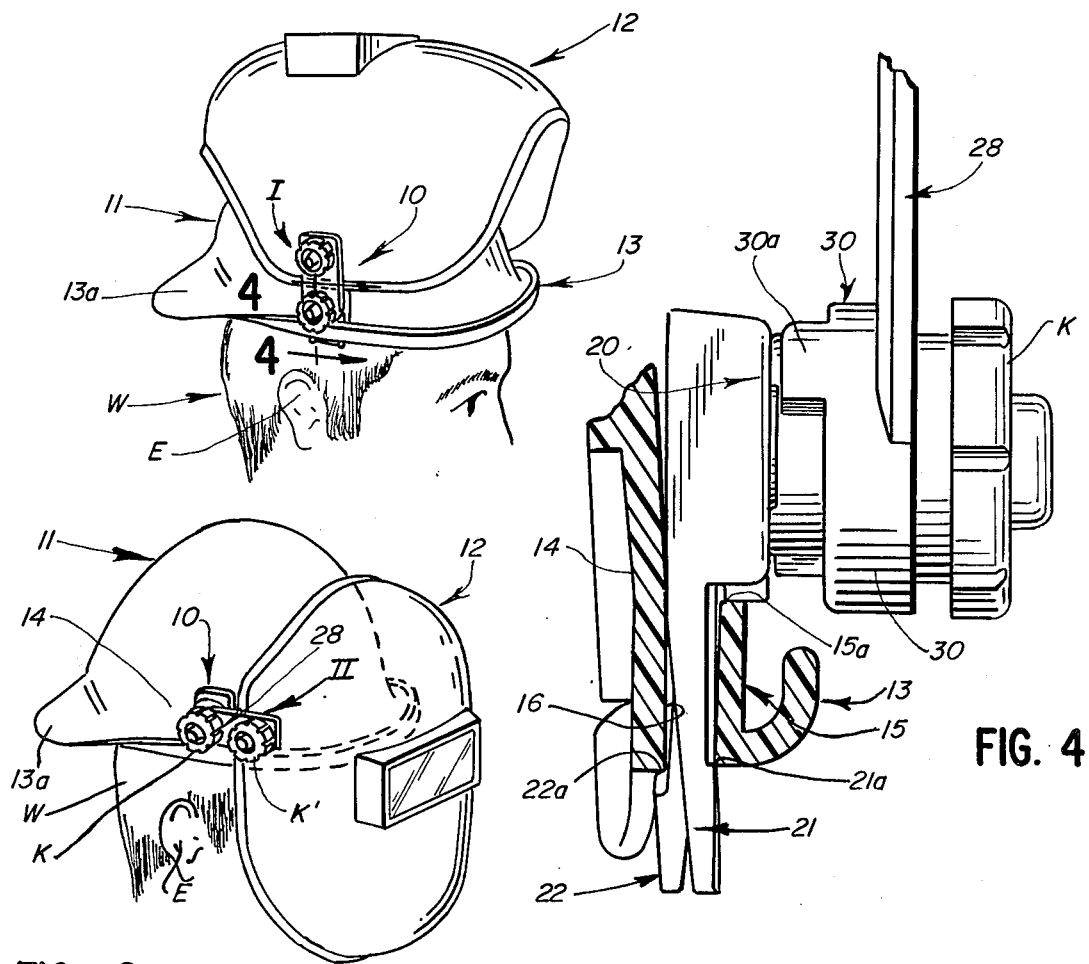
Fig. 1 is a fragmentary perspective view showing one version of the improved attaching assembly in combination with a primary unit (e.g., hard hat) and a secondary unit (e.g., welder's mask); the secondary unit is shown in an inoperative mode.
FIG. 2 is similar to FIG. 1 but showing the secondary unit in an operative mode.
FIG. 3 is an enlarged, fragmentary, exploded view of the attaching assembly shown in FIGS. 1 and 2.
FIG. 4 is an enlarged fragmentary sectional view taken along line 4—4 of FIG. 1.

Referring now to the drawings and more particularly to FIGS. 1 and 2, one form of the improved attaching assembly 10 is shown in combination with a primary unit 11 which in the illustrated embodiment is in the form of a conventional safety helmet or hard hat normally worn by construction personnel and the like, and a secondary unit 12 such as a conventional welder's mask. Other types of face and/or eye protecting devices or a telephone communication component (headphone) may be substituted for the welder's mask.

The primary unit 11 is preferably molded from a suitable impact-resistant plastic material (e.g., polypropylene). Disposed within the unit 11 and suitably connected to the interior thereof is a conventional suspension, not shown, which is adjustable to the head size of the wearer W. The lower edge of the unit is substantially delimited by a gutter-like flange 13 and a visor 13a. While FIGS. 1 and 2 show unit 11 worn with the visor 13a thereof extending to the rear, the attaching assembly, to be hereinafter described, may be utilized in the same way where the unit 11 is worn with the visor extending forwardly. Integrally formed in the exterior wall of the unit which defines a crown portion 14 and projecting laterally outwardly therefrom is a pair of shoulders 15 of like configuration, see FIG. 4. The shoulders are disposed in the vicinity of the ears E of the wearer and adjacent the unit flange 13. Each shoulder has an upwardly extending passageway 16 which normally has a substantially rectangular cross-sectional configuration. The passageway terminates at the upper end at a substantially flat surface 15a of the shoulder and at the lower end terminates at the underside of the gutter-like flange 13. The shape and dimensions of the passageways may vary from that shown in the drawings without departing from the scope of the invention herein defined.

The attaching assembly 10 as illustrated in FIG. 3 includes basically a bracket 17 and various components 18, the latter to be described more fully hereinafter. The bracket 17 as seen more clearly in FIGS. 5–9 is preferably of a one-piece construction molded from a suitable plastic material (e.g., NYLON), and includes an upright base portion 20 which rests upon and is supported by the shoulder upper surface 15a. Connected to the underside 20a of the base portion 20 and offset to one side thereof are a plurality of depending fingers or legs 21, 22, and 23, see FIG. 5. The fingers are of resilient construction and are generally arranged in side-by-side relation and adjoining fingers are separated from one another by upwardly extending slots 24. Fingers 21, 23 are the endmost fingers and extend divergently downwardly from the underside of the base portion when the bracket is disengaged from the shoulder passageway 16, see FIGS. 5 and 7. As observed in FIG. 9, the endmost fingers 21, 23 are also slightly divergent with respect to the center finger 22. The reasons for the divergency between the endmost fingers 21, 23 themselves and between the endmost fingers and the center finger 22 are to assure that there is a positive resilient engagement between the fingers and the shoulder passageway, even though the dimensions of the passageway may vary to certain extent.

The lower distal end portion of each finger is provided with a lip 21a, 22a 23a which projects outwardly in one direction and is adapted to interlockingly engage the underside of the flange 13 of the helmet 11 which is circumjacent the lower terminus of the passageway 16. It will be noted, that the upper edge of lip 22a is provided with a centrally disposed step 22'a which is adapted to engage a recess, not shown, formed in the underside of the flange of certain versions of the hard hat; also not shown. Once the lips 21a, 22a, 23a of the fingers have projected beyond the lower end of the passageway, the finger distal ends will spring outwardly relative to each other and attempt to resume their normal positions as shown in FIGS. 4 and 5 and thus, interlock with the lower end of the passageway.

To detach the bracket from the shoulder passageway 16 merely requires that the distal ends of the endmost fingers 21, 23 be manually squeezed together a slight amount and that the distal end of finger 22 be manually pushed inwardly a slight amount so that the lips formed on the distal ends do not lockingly engage the underside of the helmet flange 13. While the distal ends of the fingers are manipulated as indicated, the bracket can be readily removed from the passageway.

Besides the depending fingers, each bracket is provided with an elongated stabilizing member 25, see FIG. 5, which is pivotally attached to one side of the base portion 20 in the vicinity of the connection between the base portion and the depending fingers. In the illustrated embodiment the member 25 is attached at its midlength by a short tab 25a to the base portion. The size of the tab is such as to enable the member 25 to be tilted or distorted slightly by upper surface 15a of the shoulder 15 when the fingers have been fully extended into the passageway and are in interlocking engagement therewith as above-described. Thus, the member 25 compensates for variations in the extent of the passageway and for the configuration variations of the shoulder upper surface 15a. The underside of member 25 which resiliently engages the shoulder surface 15a is provided with a pair of depending feet 25b which are disposed at opposite ends of member 25.

Base portion 20, as seen in FIGS. 7 and 9, has the surface thereof, which is disposed adjacent the exterior surface of the crown 14 of the safety helmet 11, provided with a recessed center portion 20b having an opening 20c formed therein. The opening 20c is sized to slidably accommodate a shank portion 26a of a fastening device 26. The device 26 is provided with an enlarged head 26b which is disposed within the recessed center portion 20b when shank portion 26a is extending through opening 20c. Besides shank portion 26a, device 26 includes a second shank portion 26c having a faceted peripheral configuration and a third shank portion 26d which is externally threaded. The second and third shank portions 26c and 26d are adapted to extend through a suitable opening 27 formed in one end 28a of an elongated link member 28. The shape of opening 27 corresponds substantially to the peripheral configuration of the second shank portion 26c. The threaded shank portion 26d projects beyond the link member opening 27 and is threadably engaged by a manually adjustable knob K in a manner to be discussed more fully hereinafter.

Formed on the exposed, or outwardly facing, surface of the bracket base portion 20 and radially spaced from opening 20c is an outwardly projecting lug 20d. The lug serves as a stop to limit the pivotal movement of the link member 28 to within a predetermined sector (e.g. approximately 95°) as will be described more fully hereinafter. When the link member 28 assumes an upright position I, as shown in FIGS. 1 and 4, the secondary unit 12 is disposed in an inoperative mode. While the link member is in position I, it is at one end limit of the sector of pivotal movement. When link member 28 assumes a forwardly extending position II, it is at the opposite end limit of the sector of pivotal movement and the secondary unit is disposed in an operative mode, see FIG. 2.

The surface of the link member end portion 28a adjacent the exposed surface of the bracket base portion 20 is provided with an annular boss 30 having a pair of substantially diametrically opposed peripheral protuberances 30a which independently coact with the lug 20d formed on the bracket base portion to limit the pivotal movement of the link member in a given direction, either towards or away from position II.

In order to retain the link member 28 in either position I or II, a washer assembly 31 is provided which encompasses the threaded shank portion 26d of the fastening device 26 and is interposed the knob K and a recessed surface portion 28b of the end 28a of link member 28. The washer assembly 31, in the illustrated embodiment, includes a resilient washer 31, and a rigid washer 38 having a peripheral flange 33a which encompasses the annular periphery of washer 32. The projection of the flange 33a is less than the thickness of resilient washer 32, so that as the knob K is threaded onto shank portion 26d friction will increase between washer 32 and the recessed portion 28b of the link member 28, thereby providing greater resistance to pivoting of the link member 28 relative to the bracket base portion 20.

As seen in FIG. 3 the opposite end portion 28c of link member 28 is provided with an outwardly projecting threaded stud 28d which is adapted to extend through a suitable opening, not shown, formed in the side of the secondary unit 12. Threadably engaging stud 28d is a manually adjustable knob K'. Thus, a portion of the side of the secondary unit 12 is frictionally sandwiched between knob K' and the end portion 28c of link member 28. If desired, the portion 28e of the stud 28d adjacent the end 28c of the link member may have a faceted peripheral configuration which would conform to the shape of the opening in the side of the secondary unit 12 through which the stud extends.

In certain instances where the secondary unit 12 is in the form of a telephone headphone, the link member 28 may be omitted and the side of the secondary unit secured directly to the exposed surface of the bracket base portion by the knob K being threaded onto shank portion 26d. In the latter situation, lug 20d may be omitted from the exposed surface of the base portion.

As aforementioned, the shape, size, and type of the secondary unit 12 as well as the primary unit 11 and of the various components comprising the attaching assembly may vary from that shown without departing from the scope of the invention. Furthermore, in certain instances only one attaching assembly might be required to attach the primary and secondary units.

Thus, it will be seen that a simple, compact and inexpensive attaching assembly has been provided which requires a minimum amount of manual effort to attach or detach the assembly with respect to the primary unit. The improved attaching assembly enables the secondary unit to be moved between operative and inoperative modes by manually engaging the secondary unit or by merely jerking the head of the wearer forwardly or rearwardly, whichever the case may be.

I claim:

1. An assembly for use in attaching a secondary unit to a primary unit wherein the latter is provided with an exterior wall surface, and a shoulder projecting outwardly from the wall surface and provided with an upwardly extending passageway; said assembly comprising at least one removable bracket having a base portion adapted to rest upon and be supported by the shoulder, and a plurality of fingers connected to and depending from said base portion for insertion into a resilient engagement with the shoulder passageway and effect retention of said bracket in assembled relation with the primary unit; and adjustable means coacting with said bracket base portion for connecting the secondary unit thereto; said base portion having a surface thereof adjacent the exterior wall surface of the primary unit provided with a recess portion having an opening formed therein through which extends a portion of a first fastening component and terminates outwardly of said base portion; a second fastening component is manually adjustable on the outwardly extending portion of said first fastening component, said fastening components coacting with one another for frictionally sandwiching a segment of the secondary unit between an exposed surface of said base portion and said second fastening component.

2. An assembly for use in attaching a secondary unit to a primary unit wherein the latter is provided with an exterior wall surface, and a shoulder projecting outwardly from the wall surface and provided with an upwardly extending passageway; said assembly comprising at least one removable bracket having a base portion adapted to rest upon and be supported by the shoulder, and a plurality of fingers connected to and depending from said base portion for insertion into a resilient engagement with the shoulder passageway and effect retention of said bracket in assembled relation with the primary unit; and adjustable menas coacting with said bracket base portion for connecting the secondary unit thereto; said base portion including stabilizing means disposed adjacent the connection of the depending fingers to said base portion and provided with an elongated member having a first segment connected to the base portion and a second segment adapted to resiliently engage the shoulder surface portion circumjacent the passageway upper end.

3. The assembly of claim 2 wherein the first segment of the stabilizing means elongated member is disposed intermediate end segments of said elongated member; at least one end segment forming the second segment and being adapted to resiliently engage the shoulder surface portion circumjacent the passageway upper end.

* * * * *